US007785826B2

(12) United States Patent
Ehlers et al.

(10) Patent No.: US 7,785,826 B2
(45) Date of Patent: Aug. 31, 2010

(54) METHOD FOR THE DEACYLATION OF LIPOPEPTIDES

(75) Inventors: Eberhard Ehlers, Hofheim (DE); Heinrich Decker, Eppstein (DE); Sebastian Rissom, Hofheim (DE); Guido Seidel, Frankfurt am Main (DE); Reiner Olliger, Bruchkobel (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 332 days.

(21) Appl. No.: 11/758,207

(22) Filed: Jun. 5, 2007

(65) Prior Publication Data

US 2008/0076149 A1    Mar. 27, 2008

Related U.S. Application Data

(63) Continuation of application No. PCT/EP2005/013336, filed on Dec. 13, 2005.

(30) Foreign Application Priority Data

Dec. 15, 2004    (DE) .................. 10 2004 060 750

(51) Int. Cl.
*C12P 21/06* (2006.01)
(52) U.S. Cl. .................. 435/68.1; 435/195; 435/325
(58) Field of Classification Search ............. 435/68.1, 435/195, 325
See application file for complete search history.

(56) References Cited

U.S. PATENT DOCUMENTS

| 4,293,482 | A | * | 10/1981 | Abbott et al. ............... 530/317 |
| 5,573,936 | A | | 11/1996 | Kreuzman et al. |
| 6,194,383 | B1 | | 2/2001 | Hammann et al. |
| 6,511,962 | B1 | | 1/2003 | Borders et al. |
| 7,005,417 | B1 | | 2/2006 | Corbier et al. |
| 7,022,669 | B1 | | 4/2006 | Fauveau et al. |

FOREIGN PATENT DOCUMENTS

| EP | 0460882 | 12/1991 |
| WO | WO 00/34315 | 6/2000 |
| WO | WO 00/75177 | 12/2000 |
| WO | WO 00/75178 | 12/2000 |

OTHER PUBLICATIONS

Kreuzman et al. J. Industrial Microbiol. Biotechnol. (2000) 24: 173-180.*
Boeck, L.D., et. al., Deacylation of A21978C, An Acidic Lipopeptide Antibiotic Complex, by Actinoplanes Utahensis, The Journal of Antibiotics vol. XLI, No. 8, pp. 1085-1092 (1988).
Kimura, Y., et. al., Polymyxin Acylase: Purification and Characterization, with Special Reference to Broad Substrate Specificity, Agric. Biol. Chem., vol. 53, No. 2, pp. 497-504, (1989).
Yasuda, N., et. al., Polymyxin Acylase: An Enzyme Causing Intramolecular N2-N6 Acyl Transfer in N-Monooctanoyl-L-Lysine, Agric. Biol. Chem., vol. 53, No. 12, pp. 3245-3249, (1989).

* cited by examiner

*Primary Examiner*—Sandra Saucier
*Assistant Examiner*—Susan Hanley
(74) *Attorney, Agent, or Firm*—Jiang Lin

(57) ABSTRACT

The invention relates to a method for the enzymatic elimination of the N-acyl side chain from lipopeptides to form the corresponding nucleus, wherein the lipopeptide is prepared by fermentation, the lipopeptide being bound to the cells of the biomass, and the biomass is removed with the adhering lipopeptide, the biomass with the adhering lipopeptide is resuspended in an aqueous system, a suitable deacylase is added in dissolved or solid form to the suspension of the biomass, and the corresponding nucleus is formed, and the nucleus is optionally isolated and purified, wherein the lipopeptide obtained by fermentation is reacted after the end of the fermentation as cell-bound biomass without further purification directly with a deacylase, whereby the N-acyl chain linked via an amide linkage is eliminated.

12 Claims, No Drawings

METHOD FOR THE DEACYLATION OF LIPOPEPTIDES

This application is a continuation of PCT/EP05/13336, filed Dec. 13, 2005 which claims priority to German Application No. 102004060750.8, filed Dec. 15, 2004.

FIELD OF THE INVENTION

The invention relates to a method for the enzymatic elimination of the N-acyl side chain from lipopeptides to form the corresponding nucleus.

BACKGROUND OF THE INVENTION

Lipopeptides are cyclohexapeptides, which can be obtained by fermentation, and have a systemic antifungal activity entailing inhibition by them of (1,3)-β-D-glucan synthase, a key enzyme in fungal cell wall biosynthesis. Lipopeptides also have antibacterial activity (Exp. Opin. Invest Drugs 2000, 9, 1797-1813). It is known that lipopeptides have unfavorable physicochemical properties, such as slight solubility in water or instability in alkaline solution. In addition, natural lipopeptides show severe side effects such as damage to the venous endothelium, destruction and inflammation of tissues or local toxic effects at the site of administration.

There is thus a need to synthesize novel lipopeptides having improved pharmacokinetic and chemotherapeutic properties as well as lower toxicity. Such semisynthetic modifications generally consist of introducing acidic or basic groups into the molecular structure and of replacing the natural aliphatic side chain acid by aromatic acyl components. Modification of the fatty acid side chain (N-acyl side chain) in particular has central importance in partial syntheses of lipopeptides. This generally takes place by eliminating the N-acyl side chain of lipopeptides by enzymatic means using a natural, cell-associated or recombinant deacylase of broad substrate specificity, and reacylating the resulting peptide ring, called the nucleus, with a modified activated acid (for example EP 1 189 932; EP 1 189 933).

European patent application EP 0 460 882 describes the deacylation of the lipidic acyl position of lipopeptides using purified echinocandin B decylase. The enzyme is produced by fermentation of *Actinoplanes utahensis* (NRRL12052), it being in cell-associated form after the fermentation, and initially being detached from the cells by salt treatment before the dissolved enzyme obtained in this way is purified in an eight-stage method.

Enzymatic elimination of side chains from lipopeptides generally takes place by mixing the purified lipopeptide with a culture or a culture supernatant of a microorganism which produces a deacylase of broad substrate specificity. This may be a natural *Actinoplanes utahensis* strain (e.g. NRRL 12052; WO00/75177 and WO00/75178) or a recombinant deacylase producer such as, for example, a recombinantly modified *Streptomyces lividans* strain. A further alternative method is to add a purified deacylase to a solution or suspension of the purified lipopeptide. After the side chain has been eliminated, the reaction supernatant is freed of insoluble constituents, and the water-soluble nucleus present in the filtrate is purified. This procedure using purified or partially purified substrates is time-consuming and inapplicable on the industrial scale.

SUMMARY OF THE INVENTION

The present invention relates to a method for the enzymatic elimination of the N-acyl side chain from lipopeptides to form the corresponding nucleus, where
(a) the lipopeptide is prepared by fermentation, the lipopeptide being bound to the cells of the biomass, and the biomass is removed with the adhering lipopeptide,
(b) the biomass of fermentation step (a) with the adhering lipopeptide is resuspended in an aqueous system,
(c) a suitable deacylase is added in dissolved or solid form to the suspension of the biomass from step (b), and the corresponding nucleus is formed, and
(d) the nucleus is optionally isolated and purified, wherein the lipopeptide obtained by fermentation in step (a) is reacted after the end of the fermentation as cell-bound biomass without further purification directly with a deacylase in step (c), whereby the N-acyl chain linked via an amide linkage is eliminated.

Optionally, in a further step (e), the nucleus is reacted with an acid derivative to give a semisynthetic lipopeptide of the formula, with the amide function resulting therefrom being substituted by a phenyl-($C_5$-$C_8$)heteroaryl-phenyl, C(O)-biphenyl or C(O)-terphenyl group.

DETAILED DESCRIPTION

The present invention further relates to a method for the enzymatic elimination of the N-acyl side chain $R_{11}$ from lipopeptides of the formula (I)

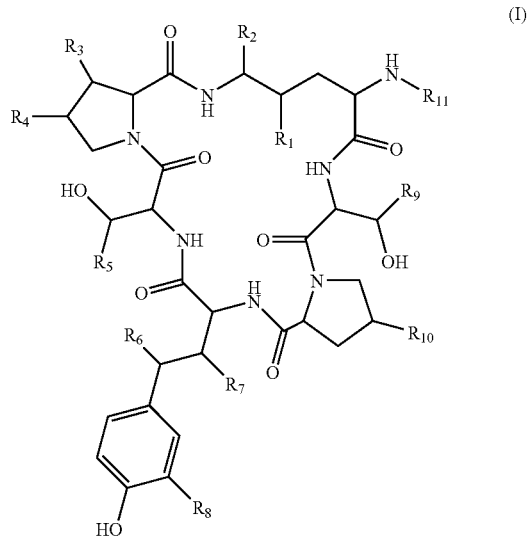

where $R_1$ is H, OH or $NR_xR_y$, where $R^x$ and $R_y$ are independently of one another H or ($C_1$-$C_6$) alkyl, $R_2$=H, OH, $NH(CH_2)_2NH_2$, $R_3$=H, OH, $R_4$=H, Me, $NH_2$, —NH—C(=NH)$NH_2$, $R_5$=H, Me, $CH_2$—C(=O)$NH_2$, $CH_2CH_2NH_2$, $R_6$=H, OH, $R_7$=H, OH, $R_8$=H, $OSO_3H$, $OSO_3Na$, NH—C(=O)$CH_2NH_2$, $R_9$=Me, and $R_{10}$=H, OH, $R_{11}$=a C(O)—($C_6$-$C_{24}$)alkyl group, a C(O)—($C_6$-$C_{24}$)alkenyl group, a C(O)—($C_6$-$C_{24}$)alkadienyl group, or a C(O)—($C_6$-$C_{24}$)alkatrienyl group, to form the corresponding nucleus of the formula (II)

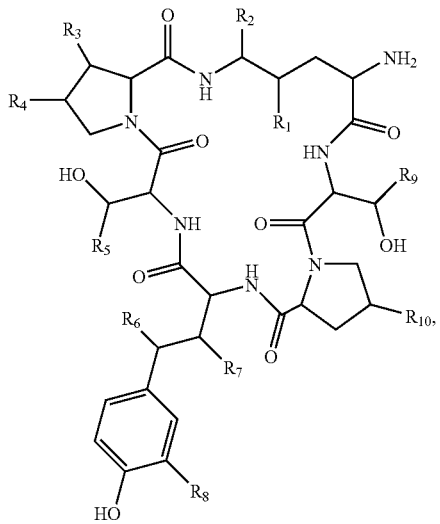

where $R_1$-$R_{10}$ have the meaning mentioned for formula (I), and where alkyl, alkenyl, alkadienyl and alkatrienyl groups where present in compounds of the formula (I) and (II) may be branched or straight-chain, where
(a) the lipopeptide of the formula (I) is prepared by fermentation, the lipopeptide being bound to the cells of the biomass, and the biomass is removed with the adhering lipopeptide,
(b) the biomass of the fermentation step (a) with the adhering lipopeptide is resuspended in an aqueous system,
(c) a suitable deacylase is added in dissolved or solid form to the suspension of the biomass from step (b), and the corresponding nucleus of the formula (II) is formed, and
(d) the nucleus is optionally isolated and purified, wherein the lipopeptide obtained by fermentation in step (a) is reacted after the end of the fermentation as cell-bound biomass without further purification directly with a deacylase in step (c), whereby the N-acyl chain linked via an amide linkage is eliminated.

The present invention further relates to a method for the enzymatic elimination of the N-acyl side chain $R_{20}$ from lipopeptides of the formula (III)

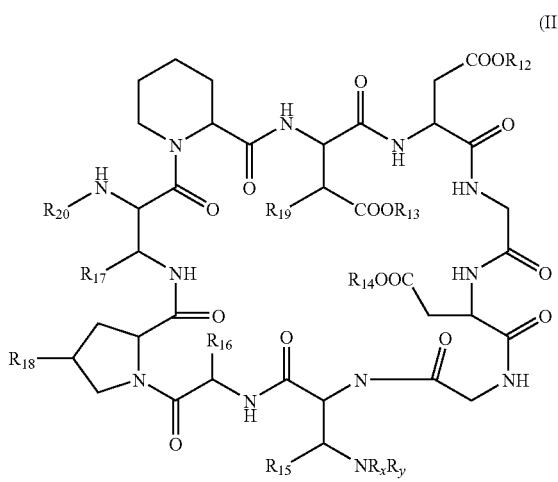

where
$R_{12}$, $R_{13}$, $R_{14}$, $R_{15}$, $R_{16}$, $R_{17}$, $R_{18}$, $R_{19}$, $R_x$ and $R_y$ are independently of one another H or ($C_1$-$C_6$)alkyl, and
$R_{20}$=a C(O)—CH(CH$_2$COR$_{21}$)—NH—CO—(C$_6$-C$_{24}$)alkyl group, a C(O)—CH(CH$_2$COR$_{21}$)—NH—CO—(C$_6$-C$_{24}$) alkenyl group, a C(O)—CH(CH$_2$COR$_{21}$)—NH—CO—(C$_6$-C$_{24}$)alkadienyl group, or a C(O)—CH(CH$_2$COR$_{21}$)—NH—CO—(C$_6$-C$_{24}$)alkatrienyl group, where $R_{21}$ is OH or NH$_2$, to form the corresponding nucleus of the formula (IV)

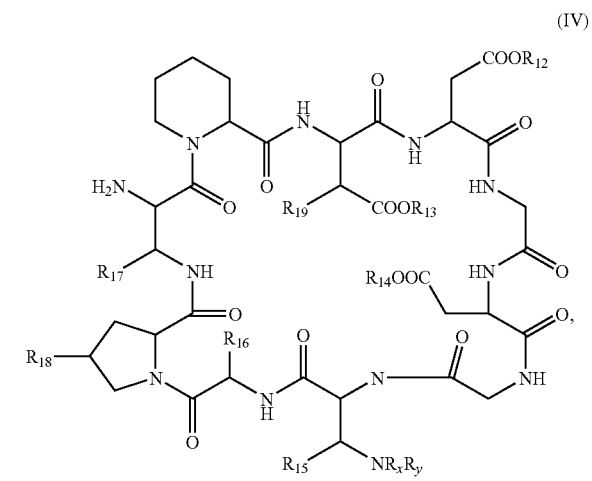

where $R_{12}$, $R_{13}$, $R_{14}$, $R_{15}$, $R_{16}$, $R_{17}$, $R_{18}$, $R_{19}$, $R_x$ and $R_y$ have the meaning mentioned for formula (III), and where alkyl, alkenyl, alkadienyl and alkatrienyl groups where present in compounds of the formula (IIII) and (IV) may be branched or straight-chain, where
(a) the lipopeptide of the formula (III) is prepared by fermentation, the lipopeptide being bound to the cells of the biomass, and the biomass is removed with the adhering lipopeptide,
(b) the biomass of the fermentation step (a) with the adhering lipopeptide is resuspended in an aqueous system,
(c) a suitable deacylase is added in dissolved or solid form to the suspension of the biomass from step (b), and the corresponding nucleus of the formula (IV) is formed, and
(d) the nucleus is optionally isolated and purified, wherein the lipopeptide obtained by fermentation in step (a) is reacted after the end of the fermentation as cell-bound biomass without further purification directly with a deacylase in step (c), whereby the N-acyl chain linked via an amide linkage is eliminated.

Optionally, the nucleus (IV) is reacted in a further step (e) with an acid derivative to give a semisynthetic lipopeptide of the formula (III') in which the group $R_{20}$ is defined as a C(O)-phenyl-(C$_5$-C$_8$)heteroaryl-phenyl, C(O)-biphenyl or C(O)-terphenyl group.

($C_1$-$C_6$)Alkyl means a hydrocarbon radical having 1, 2, 3, 4, 5 or 6 carbon atoms. Examples of ($C_1$-$C_6$)alkyl radicals are methyl, ethyl, n-propyl, isopropyl (1-methylethyl), n-butyl, isobutyl (2-methylpropyl), sec-butyl (1-methylpropyl), tert-butyl (1,1-dimethylethyl), n-pentyl, isopentyl, tert-pentyl, neopentyl, hexyl.

($C_6$-$C_{24}$)Alkyl correspondingly means a hydrocarbon radical having 6 to 24 Carbon atoms. Alkyl radicals may be straight-chain or branched. Preferred ($C_6$-$C_{24}$)alkyl radicals are fatty acid residues, for example hexyl, octyl, decanyl, undecanyl, dodecanyl, tridecanyl, tetradecanyl (myristyl), pentadecanyl, hexadecanyl, heptadecanyl, octadecanyl (stearyl), nonadecanyl, eicosanyl, dicosanyl, 9,11-dimethyltridecanyl, 11-methyltridecanyl.

The previous isolation and elaborate purification of the lipopeptide starting material is dispensed with in this procedure, because the lipopeptide bound to the biomass is employed directly in the deacylation step. The method of the invention is therefore suitable for the industrial scale. Impurities and byproducts present in the complex nutrient solution of step (a) of the method are removed in a simple manner, e.g. by filtration or centrifugation, before the deacylation takes place in step (b) of the method. Examples of impurities and byproducts are media ingredients, metabolic products of the strain or enzymes.

The biomass with adhering lipopeptide obtained in step (a) of the method is optionally washed with water before the resuspension in step (b) of the method.

The aqueous system for resuspending the cell-bound lipopeptide in step (b) of the method of the invention is water or an aqueous buffer solution, preferably with a pH of from 7.2 to 4.5, particularly preferably from 6.0 to 5.0, specifically preferably at a pH of 5.5. Buffer solutions which can be used are all those solutions known to the skilled worker. The subsequent deacylation can be carried out in the pH range from pH 4 to 9; a preferred range is from pH 4.6 to pH 7.8, with the pH optimum for the enzymic action at 6-6.2.

The method of the invention preferably relates to compounds of the formula (I) in which $R_{11}$ is

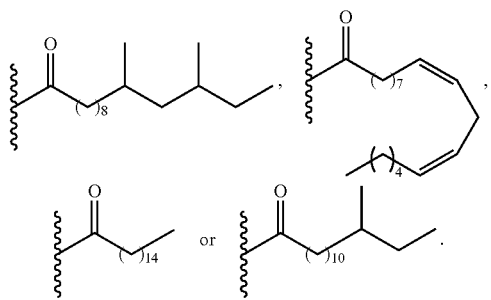

The lipopeptide starting material of the formula (I) can be obtained by fermentation. Examples of lipopeptides of the formula (I) are aculeacin (U.S. Pat. No. 4,212,858)
deoxymulundocandin (EP 438813)
echinocandin derivatives, e.g. echinocandin B, C or D (EP 1189933; FEBS Letters 1984, 173(1), 134-138)
FR901379 (Biochim. Biophys. Acta 2002, 1587, 224-233)
mulundocandin (Bioorg. Med. Chem. Lett. 2004, 14, 1123-1128)
syringomycin (FEBS Letters 1999, 462, 151-154)

It is possible and preferable to employ in the method of the invention deoxymulundocandin, echinocandin B or mulundocandin as substrate.

The provision of deacylated compounds of the formula (II) makes it possible to prepare semisynthetic lipopeptides (I') having improved pharmacological, pharmacokinetic or chemotherapeutic properties, the nucleus (II) being reacylated in a further step (e) with an acid derivative, for example an appropriate acid in the presence of dimethylaminopyridine (DMAP) in dimethylformamide (DMF) (J. Antibiot. 1999, 52(7), 674-676). For example, FK463 can be obtained from FR901379 by deacylation using FR901379 acylase via the corresponding nucleus FR179642 and subsequent acylation with an isoxazolyl-containing benzoyl side chain (Biochim. Biophys. Acta 2002, 1587, 224-233).

It is also possible for semisynthetically prepared compounds of the formula (I) to be deacylated in the method of the invention to give the corresponding compound of the formula (II).

Semisynthetic lipopeptides (I') correspond to compounds of the formula (I) but differ in the definition of the radical $R_{11}$. The radicals $R_1$-$R_{10}$ in semisynthetic lipopeptides (I') are as defined for compound (I), and the group $R_{11}$ is defined as a C(O)-phenyl-($C_5$-$C_8$)heteroaryl-phenyl, C(O)-biphenyl or C(O)-terphenyl group, where the phenyl, biphenyl, terphenyl or heteroaryl groups are unsubstituted or substituted by one or two groups selected from the group of ($C_1$-$C_{10}$)alkyl or O($C_1$-$C_{10}$)alkyl. Phenyl radicals in compounds (I') may be unsubstituted or substituted one or more times, for example once, twice or three times, by identical or different radicals. The substituent in monosubstituted phenyl radicals may be in position 2, position 3 or position 4. Disubstituted phenyl may be substituted in the 2,3 position, 2,4 position, 2,5 position, 2,6 position, 3,4 position or 3,5 position. The substituents in trisubstituted phenyl radicals may be present in the 2,3,4 position, 2,3,5 position, 2,4,5 position, 2,4,6 position, 2,3,6 position or 3,4,5 position. ($C_5$-$C_8$)heteroaryl radicals are aromatic ring compounds having a total of 5, 6, 7 or 8 atoms in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms, e.g. one nitrogen and one oxygen atom. The heteroaryl radicals may be attached via all positions, for example via the 1 position, 2 position, 3 position, 4 position, 5 position, 6 position, 7 position or 8 position. Heteroaryl radicals may be unsubstituted or substituted one or more times by identical or different radicals. Heteroaryl means for example furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl. Isoxazolyl applies in particular as heteroaryl radicals.

Compounds of the formula (I') are described for example in European patent application EP1189933.

Examples of semisynthetic lipopeptides of the formula (I') are

A-1720132 (Antimicrob. Agents Chemother. 1998, 42, 389-393)
A-192411.29 (Antimicrob. Agents Chemother. 2000, 44, 1242-1246)
caspofungin (MK-0991; Antimicrob. Agents Chemother. 1997, 41, 2326-2332)
FK463 (Antimicrob. Agents Chemother. 2000, 44, 57-62)
pneumocandins, e.g. pneumocandin A or B (Tetrahedron Lett. 1992, 33(32), 4529-4532)

It is additionally possible with the method of the invention to prepare other lipopeptides which can be obtained in principle by fermentation by deacylation/reacylation of lipopeptides (I).

A particularly preferred example of a lipopeptide (I) is deoxymulundocandin (V)

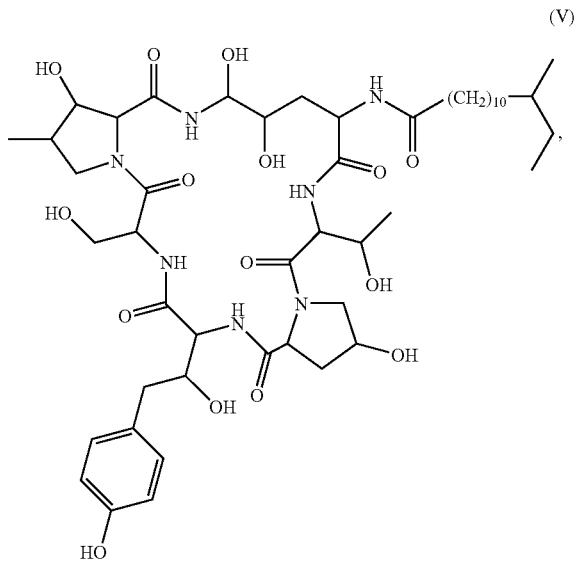

where the deoxymulundocandin nucleus (VI) is prepared in the method of the invention by deacylation starting from deoxymulundocandin (V):

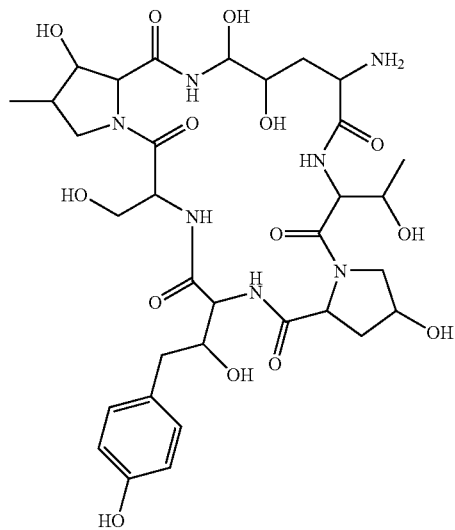

Lipopeptides of the formula (III) are disclosed in European patent applications EP629636 and EP1068223.

The method of the invention preferably relates to compounds of the formula (III), in which $R_{12}$, $R_{13}$, $R_{14}$, $R_{15}$, $R_{16}$, $R_{17}$, $R_{18}$, $R_{19}$, $R_x$ and $R_y$ are equal to H.

The method of the invention further preferably relates to compounds of the formula (III) in which $R_{20}$ is

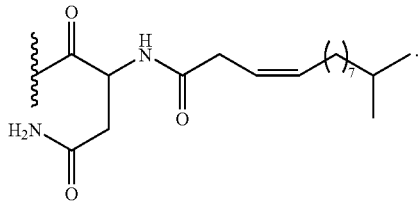

A particularly preferred example of a lipopeptide (III) is the compound of the formula (VII)

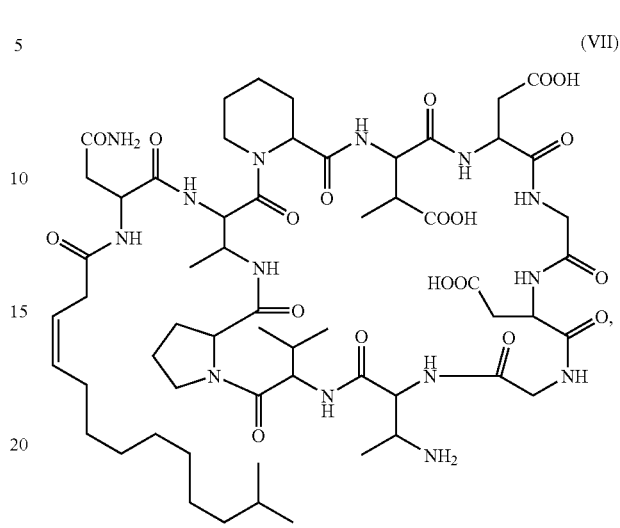

where the corresponding nucleus (VIII) is prepared by deacylation:

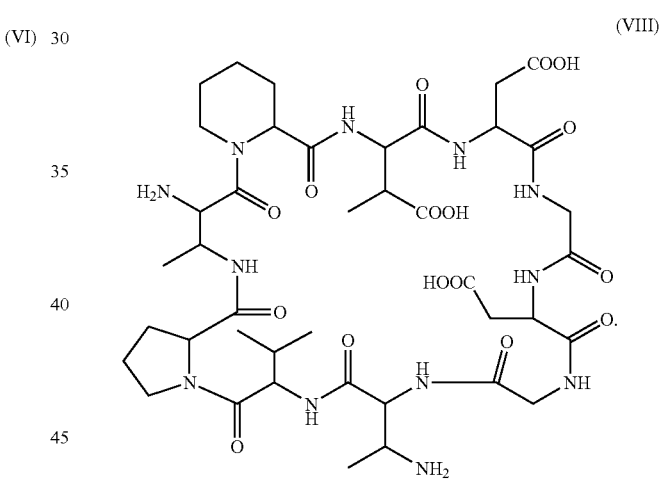

One advantage of the method of the invention is that an impure lipopeptide (I) or (III) still adhering to the biomass is used in aqueous suspension as substrate for the deacylation, purification of the starting material is superfluous, and thus production of the nucleus (II) or (IV) is possible on the industrial scale.

Natural enzymes with a broad range of action are employed in pure or partially purified form for the deacylation. Examples of deacylases are echinocandin B (EGB) deacylase, which is obtained by cultivation of an *Actinoplanes utahensis* species (La Verne et al., J. Antibiotics 1989, 42, 382-388), or polymyxin deacylase (161-16081 Fatty Acylase, Pure; 164-16081 Fatty Acylase, Crude; Wako Pure Chemical Industries, Ltd.). The ECB deacylase from *Actinoplanes utahensis* can likewise be cloned and expressed in *Streptomyces lividans*. It is preferred to prepare a recombinant enzyme of broad substrate specificity in a transformed *Streptomyces lividans* strain, because significantly higher enzyme yields can be achieved in this way. The deacylase can be added in isolated form as solution or as solid to the biomass of the lipopeptide fermentation in step (c), and is preferably prepared and concentrated separately beforehand. Methods for purifying lipopeptide deacylase from *Actinoplanes utahensis* are disclosed in the literature (see EP460882). The deacylation is carried out by standard methods. For example, the deacylation is carried out with polymyxin acylase as described by Yasuda et al, Agric. Biol. Chem., 53, 3245 (1989) and Kimura, Y., et al., Agric. Biol. Chem., 53, 497 (1989).

Example 1

Preparation of the Recombinant Deacylase Producer

A DNA fragment coding for the deacylase was isolated from the strain *Actinoplanes utahensis* NRRL 12052. The fragment was cloned (plasmid pCS1) and subcloned (plasmid pCS2), and the plasmid pCS2 was transformed into a *S. lividans* strain. Spore suspensions were prepared from a single colony of the recombinant *S. lividans* strain and were stored in ampoules at −20° C.

Cloning of the deacylase: the chromosomal DNA from *Actinoplanes utahensis* NRRL 12052 was isolated, digested with EcoRI and BglII and separated on an agarose gel, and DNA fragments with a length of 7-9 kb were isolated and cloned into the plasmid pUC19 (EcoRI/BamHI cleavage site). The ligation was transformed into *E. coli*, and 250 resulting ampicillin-resistant clones (50 µg/ml) were investigated by PCR. The primers were synthesized on the basis of the published DNA sequence of the deacylase (see GenBank Nucleotide Sequence Database Accession Number D90543; J. Inokoshi et al, Gene 1992, 119, 29-35).

The plasmid pCS1 comprises the 8 kb EcoRI/BglII fragment which is sought from *A. utahensis* NRRL 12052. This was also confirmed by restriction digestion of the fragment and comparison with the literature data (see J. Inokoshi et al, Gene 1992, 119, 29-35). The plasmid pCS1 was digested with EcoRI/HindIII, and the 8 kb fragment with the acylase was cloned into the plasmid pWHM3 (EcoRI/HindIII cleavage site; see J. Vara et al, J. Bacteriology 1989, 171, 5872-5881) and transformed into *E. coli*. The transformants were selected with ampicillin (50 µg/ml). The resulting plasmid pCS2 comprises the 8 kb EcoRI/HindIII fragment with the deacylase.

The plasmid pCS2 was then transformed by polyethylene glycol (PEG) protoplast transformation into the strain *Streptomyces lividans* TK64 JT46, plated out on R2YE medium (Kieser et al., Practical *Streptomyces* Genetics, The John Innes Foundation, 2000, page 408), and clones were selected with thiostreptone after 24 hours (20 µg/ml). Resulting thiostreptone-resistant transformants were isolated (in medium 1) and their productivity was tested in TSB medium in shaken flasks. Spore suspensions were then prepared from a positive clone (medium 1) and were stored in 20% glycerol at −20° C. General molecular biology methods (ligation, transformation, PCR, restriction digestion, agarose gels) can be read up in Sambrook et al. (in "Molecular Cloning", Cold Spring Harbor Laboratory Press, Second Edition, 1989, ISBN 0-87969-906-6), and methods for isolating chromosomal DNA from *actinomyces* and transformation of *Streptomyces lividans*, specific methods for PCR of DNA from *actinomyces*, and regeneration of the protoplasts are to be found in Hopwood et al. (in "Practical *Streptomyces* Genetics", The John Innes Foundation, 2000, ISBN 0-7084-0623-8).

Medium 1 mentioned in the preceding section comprises the following ingredients:

| | |
|---|---|
| Malt extract | 10 g/L |
| Yeast extract | 4 g/L |
| Glucose | 4 g/L |
| Agar | 15 g/L |
| pH | 7.2 |

Example 2

Preparation of the Deacylase by Fermentation

A recombinant *Streptomyces lividans* strain as described in Example 1 was used to produce the enzyme. Such a strain can be cultivated in a batch or fed-batch fermentation. The normal process chain comprised a preculture (TSB medium) in a shaken flask, which was incubated at 28° C. and 220 rpm for three days. This flask can be used for direct inoculation of a fermenter of up to 2000 L (0.15-6% v/v inoculum). It is also possible as an alternative to insert a second preculture on the 10-50 L scale into the process chain in order, by increasing the inoculum, to speed up the initial rate of growth in the main stage.

Preparation of the enzyme by fermentation: the Spores were Reactivated by Slowly thawing a tube of an ampoule. 200 µl of the resulting suspension were used for sterile inoculation of an Erlenmeyer flask which contained 500 ml of the following medium [plus 10 µg/ml thiostreptone (50 mg/ml DMSO)]:

Preculture medium: TSB medium (Soybean-Casein-Digest Medium U.S.P.; ready prepared medium; OXOID LTD, England; product-no. CM129)

| Substance | Concentration [g/L] |
|---|---|
| Casein (digest) | 17 |
| Soybean meal (digest) | 3 |
| NaCl | 5 |
| $K_2HPO_4$ | 2.5 |
| Glucose | 2.5 |
| Water | ad 500 ml | pH: 7.3±0.02,

Sterilization: 20 min, 121° C., 1 bar,

Incubation: 3 days; 28° C. and 220 rpm (excursion: 2.5 cm).

At the end of the preculture, it was transferred in accordance with the stated inoculum into a fermenter which contains the following medium:

Main Culture Medium:

| Substance | Concentration [g/L] |
|---|---|
| $(NH_4)_2SO_4$ | 21 |
| $K_2HPO_4$ | 1 |
| Sodium glutamate | 5 |
| $CaCl_2$ | 1 |
| 50× mineral salt solution 1 | 20 ml |
| Desmophene 3600 | 1 ml |
| Glucose | 40 |
| Citric acid | 3.75 mg |

The mineral salt solution 1 added to the main culture medium has the following composition:

Mineral Salt Solution 1:

| Substance | Concentration [g/L] |
|---|---|
| $MgSO_4 * 7H_2O$ | 28.9 |
| $FeSO_4 * 7H_2O$ | 0.5 |
| $ZnSO_4 * 7H_2O$ | 0.5 |
| $MnSO_4 * 7H_2O$ | 0.1 |
| $CuSO_4 * 7H_2O$ | 0.05 |
| $CoCl_2 * 6H_2O$ | 0.04 |

The medium can be sterilized with direct steam or in an autoclave (at 121-125° C. and 1.1-1.2 bar). The pH after the sterilization was about pH 6.5. The carbon source was added separately under sterile conditions, whereupon the pH fell further to about pH 6. After the medium had been made up to the desired volume, the following fermentation conditions were maintained during the fermentation:

Temperature: 25-33° C., preferably 28° C.,

Pressure: 0.5-1 bar, preferably 0.5 bar

Stirrer tip speed: 1-2 m/s,

Aeration: 0.25-1.5 vvm, preferably 0.5 vvm, pO2: >10% (controlled)

pH controlled at 6.5-7.2 with phosphoric acid and/or sodium hydroxide solution, preferably pH 7.0 (controlled).

An antifoam can optionally be employed, for example a branched polyester containing hydroxyl groups, preferably Desmophene® (Bayer Material Science, Leverkusen, Germany).

The carbon source was consumed after about 100 hours, and between 50-150 U/L were present in the fermentation solution.

After setting these parameters and inoculation with the desired inoculum volume, the productivity maximum was reached after 72-120 hours. Expression of the enzyme was coupled to growth and required no induction. Expression and production of the enzyme were monitored by employing an offline rapid assay (see Example 3) for determining the enzymic activity. The fermentation was stopped at the time of maximum productivity. It was possible by using a fed-batch method to increase considerably the productivity and the space-time yield. Preferably used for this purpose was a glucose solution (1-5 g/l*h) in the fed-batch method with a simultaneous increase in the power input via the stirrer speed ($pO_2$ control >10%).

Example 3

Deacylase Activity Determination

To monitor the enzymic activity during the preparation of the deacylase by fermentation, during the isolation of the enzyme or during the enzymatic side-chain elimination from lipopeptides such as deoxymulundocandin, the following enzymatic rapid assay was used:

20 μL of a sample containing the deacylase are added to 500 μL of a solution, preheated to 60° C., of 2.5 g/L deoxymulundocandin (V), 0.5% v/v Brij 35 in 200 mM sodium phosphate buffer (pH 5.5). The solution is incubated at 60° C. with shaking for 10 minutes. The deacylation is then stopped by adding 480 μL of 0.85% v/v phosphoric acid.

After centrifugation and removal of insoluble constituents, the amount of the deoxymulundocandin nucleus (VI) formed is determined in an accompanying HPLC analysis. For this purpose, 5 μL of the solution are injected onto a Merck Purospher Star RP column (4*55 mm) and eluted with a three-minute linear gradient of 4→20% v/v acetonitrile acidified with 0.1% v/v phosphoric acid at a flow rate of 2.5 ml/min. Detection takes place at λ=220 nm. The nucleus has a retention time of 1.4 minutes. Quantification takes place by means of an external standard.

One unit (U) of deacylase activity is defined as the amount of enzyme which, under the described analysis conditions, is required to produce 1 μmol of deoxymulundocandin nucleus in one minute.

Highly concentrated enzyme samples like those for example resulting during the isolation of the deacylase are diluted with 200 mM sodium phosphate buffer (pH 5.5) to a concentration of 5-200 U/mL which can be accurately quantified in the enzymic assay. For enzyme samples which contain deoxymulundocandin or the deoxymulundocandin nucleus, an analogous substrate, for example the compound (VII), is used in the rapid assay. The resulting nucleus (VIII) is detected at a retention time of 2.4 minutes.

Example 4

Isolation of the Deacylase

To isolate the enzyme, the supernatant of culture solutions prepared as described above was separated off by methods known per se, preferably centrifugation, and then concentrated, for example by ultrafiltration. For example, after the fermentation is complete, culture solutions (about 2000 L) of the recombinant *Streptomyces lividans* strain are killed where appropriate with suitable disinfectants, and the supernatant containing the enzyme is separated off in a separator (e.g. Westfalia SC 35 type) at a throughput of 1000-1300 l/h. The separated biomass was discarded. The quality of the solid-liquid separation can be tested by measuring the optical density at λ=540 nm in the clear effluent. The clarified supernatant is preferably concentrated by a concentration factor of about 10-20 compared with its original volume by using polyether-sulfone membranes with a nominal cutoff of 10-50 kDa, preferably of 20 kDa. The circulation flow rate was 4500 l/h with a transmembrane pressure of 2.5-3.5 bar; the permeate flow rate fell during the filtration from the initial 20-30 $l/hm^2$ to 4-10 $l/hm^2$. The permeate was discarded.

The aqueous enzyme concentrates (retentates) could be stored in the cool in this form and then employed directly for deacylation of lipopeptides.

As an alternative to this it was also possible to precipitate the enzyme by adding 2-propanol to a final concentration of 40-60% v/v, preferably 50-55% v/v. The precipitation can be carried out in the temperature range of 0-25° C., preferably in the range of 4-10° C., particularly preferably 6° C. The deacylase can also be precipitated with acetone instead of 2-propanol, but 1-propanol is less suitable as precipitating agent. The supernatant was decanted and then the enzyme was removed by centrifugation from the remaining suspension after the precipitation was complete (e.g. using a CEPA tube centrifuge) and was stored in moist form in the cool until further use.

The moist enzyme, which results as pellets, was dissolved in a phosphate buffer of suitable concentration. Insoluble constituents are filtered off. The clear filtrate was employed directly after the activity determination for deacylation of deoxymulundocandin.

The precipitate can also be stored stably after previous addition of additives such as salts (for example ammonium sulfate), sugars (e.g. glucose) or sugar alcohols such as sorbitol or mannitol in lyophilized form over a prolonged period. The use of an enzyme precipitate is preferred because *Streptomyces lividans* fermentation media components can be eliminated in this way before the side-chain elimination.

Example 5

Preparation of Lipopeptides by Fermentation

Cyclic peptides of the formula (II), also called nucleus, were prepared by obtaining by fermentation beforehand the appropriate lipopeptides of the formula (I) to be used as substrate (exocyclic N-acyl derivatives of the nucleus) by cultivating the relevant microorganisms. For example, the water-insoluble deoxymulundocandin (V) adhering to the biomass is obtained by cultivating *Aspergillus sydowii* as described in European patent application 0 438 813 A1 and is presented once again below: Deoxymulundocandin was produced by growing a producer of *Aspergillus sydowii*, preferably a producer selected by conventional strain improvement, in a batch fermentation process. Deoxymulundocandin is a classical secondary metabolite which is formed only after fermentation has lasted about three days:

The deoxymulundocandin-producing *Aspergillus sydowii* strain was grown as preculture in an Erlenmeyer flask. The flasks were inoculated with 1 ml of a spore suspension directly from the ampoule. The following parameters were maintained: T=28° C.; 240 rpm, 48-72 hours.

The preculture medium employed was:

| Substance | Amount [g/L] |
|---|---|
| Corn steep powder | 0.5 |
| $CaCO_3$ | 2 |
| Yeast extract | 2 |
| Glucose | 5 |
| NaCl | 5 |
| Soybean flour | 15 |
| Pharmamedia | 15 |
| Desmophene | 3 ml/L |

The pH after sterilization of the medium was pH 6.9 and at the end of the culture was pH 7-7.5. The PMV (percent mycelial volume) was between 15-20%. For an industrial process, a second preculture was fermented under the same conditions and with the same medium.

The main fermenter was inoculated with an inoculum of 1-6% from a shake culture or a prefermenter and contained the following medium:

Main Culture Medium (MF3)

| Substance | Proportion [%] |
|---|---|
| Yeast extract | 0.930 |
| Soybean flour | 1.430 |
| Pharmamedia | 1.475 |

-continued

| Substance | Proportion [%] |
|---|---|
| Soluble starch | 4.300 |
| $CaCO_3$ | 0.400 |
| $MgSO_4 \cdot 7H_2O$ | 0.070 |
| Desmophene | 0.200 |
| Glucose | 1.000 |
| Standard trace element solution | 1 ml/L |

Fermentation Parameters:

Inoculation density: 0.5-6%, preferably 1-2%,

Temperature: 25-33° C., preferably 27-30° C.,

Aeration: 0-1.5 vvm, preferably 0.5-0.8 vvm,

Stirrer tip speed: 1.4 m/s (depending on the stirrer used)

The fermentation was carried out at T=25-35° C., preferably at 28-32° C. A slight gage pressure of 0.2-1 bar was applied and the dissolved oxygen concentration was continuously controlled at >30%. A cascade of increasing stirrer speed (starting at 95 rpm, tip speed 1.2 m/s) and increasing aeration rate (starting at 0.2 $N/m^3$) was preferably used for this. It was unnecessary to control the pH during the fermentation. However, it serves to improve the robustness of the process. The pH was in the range of 5.5-7; preferably 6.2-6.5. The pH was controlled at pH 6.5 with sulfuric acid from hour 24-30 onwards. Various antifoams can be used to avoid foaming, with preference for Desmophene 3600 or Hodag AFM-5. For production of deoxymulundocandin, a preferred morphology throughout the fermentation process is desirable. This small pellet-form growth is influenced by the choice of the stirrer; a disk agitator is particularly suitable for pellet-like growth.

The total fermentation time may be more than 240 hours, with the product formation rate being reasonably constant over a long period, and the end of fermentation being established by an accompanying offline analysis. The product concentration at the end of a fermentation was in the range of 800-1200 mg/l deoxymulundocandin.

Before harvesting the biomass, the pH is adjusted to a pH of from 6.5 to 5.5, preferably pH 6.0, the stability optimum of deoxymulundocandin.

Example 6.1

Deacylation of Lipopeptides to the Corresponding Nucleus (1)

After the fermentation was complete, the culture broth was separated into culture supernatant and biomass. Various conventional filtration and separation techniques can be used for this purpose. A filter press is preferably used. The biomass was washed on the filter press where appropriate once with water and then transferred for the deacylation into a reaction container. Filtrate and washing water were discarded.

The biomass was then resuspended together with the adherent lipopeptide in water, preferably in 1-2 times the amount of water. For example, after the deoxymulundocandin fermentation was complete, 30-50 kg of wet biomass were resuspended in 100-150 liters of water, the initial deoxymulundocandin concentration for the deacylation being between 0.5-1.5 g/L. The suspension was stirred until a homogeneous paste was obtained.

The suspension was adjusted to the desired pH. For side-chain elimination, a solution of the deacylase was then added to the reaction mixture, using 20-50 units of enzyme per gram of lipopeptide, preferably 25-40 U/g, equivalent to 25-150 U/L, preferably 25-80 U/L.

The deacylation process itself was carried out—after dissolving the enzyme in a phosphate buffer—at temperatures of 20-80° C.; a temperature range of 20-40° C. was preferred, particularly preferably 30-35° C. Higher temperatures may favor byproduct formation such as ring opening and/or dehydration. The stirrer speed in a 200 L fermenter was 100-250 rpm, preferably 120-180 rpm.

The deacylase can be employed in the pH range from pH 4 to 9; a range from pH 4.6 to pH 7.8 is preferred, with the pH optimum for the enzymic action at 5.2-6.2. Higher pH values should be avoided because in this case too there is an increase in the formation of ring-opened or dehydrated byproducts of the formulae (IX) and (X):

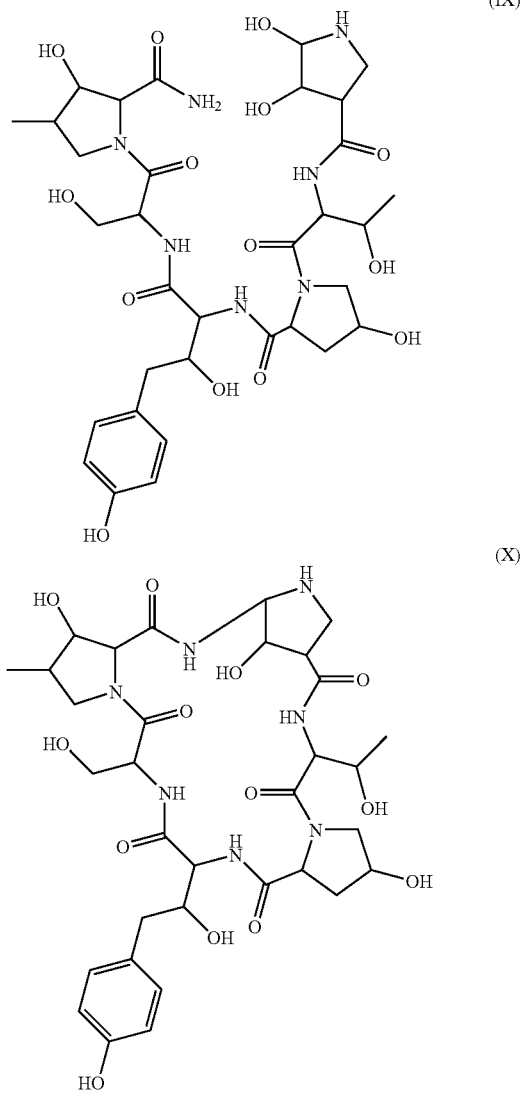

The reaction time for the deacylation reaction varies and depends greatly on the chosen pH and the chosen temperature. The end of the enzymatic elimination of the side-chain acid is determined by accompanying analytical HPLC through measurement of the nucleus formation in the reaction supernatant. For example, in a deacylation of deoxymulundocandin on the 200 L scale the deacylation was complete after 20-30 hours.

Example 6.2

Deacylation of Lipopeptides to the Corresponding Nucleus (2)

The deacylation of deoxymulundocandin was carried out as in example 6.1. The deoxymulundocandin mycelium was filtered and washed with water. This was followed by resuspension in the same volume of water and deacylation to the nucleus at pH 5.5 and 30° C.:

Culture filtrate: 160 liter

Culture filtrate-purity: 72.3 area % (HPLC)

Loading: 3.8 g/L

Main fraction: 55 liter

Main fraction purity: 95.1 area % (HPLC)

Lyophilisate nucleus: 34.1 g (yield 30%)

Lyophilisate purity: 88.0 area % (HPLC)-78.4% w/w (versus internal standard).

Example 7

Isolation and Purification of the Nucleus

After the deacylation was complete, the *Aspergillus sydowii* biomass was removed by centrifugation or filtration, adding a filtration aid where appropriate. The removed biomass was discarded. The clear filtrate, which contains the water-soluble nucleus, was subsequently purified by column chromatography. A hydrophobic polymer such as polystyrene-vinylbenzene copolymers, polyacrylates or polymethacrylates served as stationary phase. As an alternative to this, the nucleus can also be purified by cation exchange chromatography. Purification by column chromatography on a styrene-vinylbenzene copolymer as stationary phase is preferred.

Water was used as eluent (mobile phase), adding organic acids and alcohols as cosolvents to increase the selectivity. The preferred mobile phase is water containing small amounts of acetic acid and 1- or 2-propanol. Acid is added for targeted depletion of impurities which are present, such as ring-opened or dehydrated compounds.

The eluate was collected in fractions, and the fractions containing the nucleus were—after quantification by accompanying analytical HPLC—combined and concentrated by nanofiltration. The membranes employed for the nanofiltration were able to retain 50-70% sodium chloride, preferably 50% NaCl.

The resulting nucleus concentrate (retentate) was then freeze dried or spray dried. The resulting solid nucleus could be employed directly and without additional purification as starting material for the reacylation with activated aromatic side-chain acids.

Isolation and Purification of the Deoxymulundocandin Nucleus on the Industrial Scale:

After the enzymatic side-chain elimination is complete, a 1000 liter deacylation mixture is filtered through a filter press. The removed biomass is washed with water on the filter press and then discarded. Filtrate and washing water are combined and clarified again by filtration through a layer (Seitz K-200 type). The filtered solution ought to have a pH of 6-6.5. The pH should be readjusted where appropriate with 2 M acetic acid or 2 M sodium hydroxide solution.

750 liters of the clear solution, which may contain between 500-700 mg/L of deoxymulundocandin nucleus, are loaded with a linear flow rate of 100-200 cm/h onto a chromatography column which is packed with 25 liters of Amberchrom® CG161m as stationary phase. The height of the stationary phase bed is 26 cm, and the internal column diameter is 35 cm. The conductivity of the solution is not critical.

Throughout the progress of the chromatography, the absorption at λ=280 nm, the pH and the conductivity are continuously measured and recorded. The column flow-through is collected in one fraction and discarded after HPLC testing.

After loading is complete, the stationary phase is washed with purified water at a linear flow rate of 100-150 cm/h until the absorption which is continuously measured in the outflow from the column has almost reached the base line. The washing solution is collected in a single fraction and discarded after HPLC testing.

After the washing is complete, the deoxymulundocandin nucleus is eluted isocratically with 10 bed volumes at a linear flow rate of 100-150 cm/h. Water is used for the desorption, to which 0.1% v/v acetic acid and 2% v/v 2-propanol (or 1-propanol) are added to increase the selectivity. The eluate is collected in fractions of 5-25 liters, the size of the fractions being controlled via the measured and continuously recorded absorption.

Aliquots are taken from all the fractions and the purity and the content of deoxymulundocandin nucleus therein are determined by accompanying HPLC analysis. Nucleus-containing fractions with a purity of >90 area % are combined. The total eluate (50-100 liters) is then concentrated by a factor of 2-5 by nanofiltration using a membrane whose sodium chloride retention is 50%.

The resulting nucleus retentate is then sterilized by filtration and subsequently freeze dried or spray dried. Marginal fractions from the purification of the deoxymulundocandin nucleus by column chromatography can be recycled.

After complete drying, the resulting solid deoxymulundocandin nucleus is, after HPLC analysis, dispensed into suitable plastic containers. The containers are stored at −25° C. until used further.

The invention claimed is:

1. A method for the enzymatic elimination of an N-acyl side chain from a lipopeptide, wherein the lipopeptide is a cyclohexapeptide having an N-acyl side chain, to form the corresponding nucleus, comprising
   (a) preparing the lipopeptide by fermentation, the lipopeptide being bound to the cells of a biomass produced by the fermentation, and removing the biomass with the adhering lipopeptide,
   (b) resuspending the biomass with the adhering lipopeptide from step (a) in an aqueous system,
   (c) adding a suitable deacylase which is capable of cleaving an N-acyl side chain in dissolved or solid form to the suspension of the biomass from step (b), and forming the corresponding nucleus, and
   (d) optionally isolating and purifying the nucleus, wherein the lipopeptide obtained by fermentation in step (a) is reacted after the end of the fermentation as cell-bound biomass without further purification directly with the deacylase in step (c), whereby the N-acyl side chain linked via an amide linkage is eliminated.

2. The method as claimed in claim 1, wherein the lipopeptide has the formula (I)

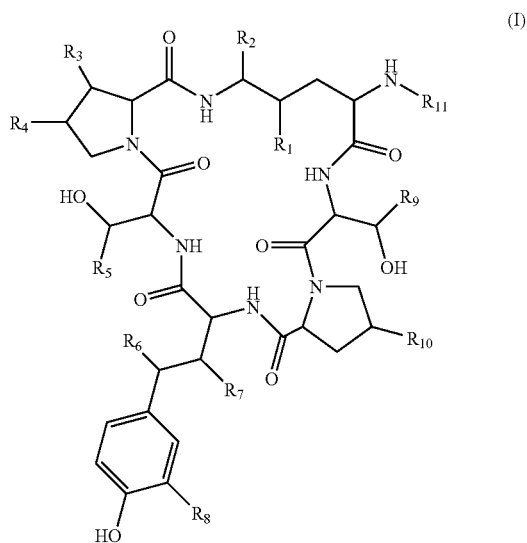

and where
$R_1$ is H, OH or $NR_xR_y$, where
  $R_x$ and $R_y$ are, independently of one another, H or ($C_1$-$C_6$) alkyl,
$R_2$ is H, OH, or $NH(CH_2)_2NH_2$,
$R_3$ is H, or OH,
$R_4$ is H, Me, $NH_2$, or —NH—C(=NH)$NH_2$,
$R_5$ is H, Me, $CH_2$—C(=O)$NH_2$, or $CH_2CH_2NH_2$,
$R_6$ is H, or OH,
$R_7$ is H, or OH,
$R_8$ is H, $OSO_3H$, $OSO_3Na$, or NH—C(=O)$CH_2NH_2$,
$R_9$ is Me,
$R_{10}$ is H, or OH, and
$R_{11}$ is a C(O)—($C_6$-$C_{24}$)alkyl group, a C(O)—($C_6$-$C_{24}$) alkenyl group, a C(O)—($C_6$-$C_{24}$)alkadienyl group, or a C(O)—($C_6$-$C_{24}$)alkatrienyl group,
to form the corresponding nucleus of the formula (II)

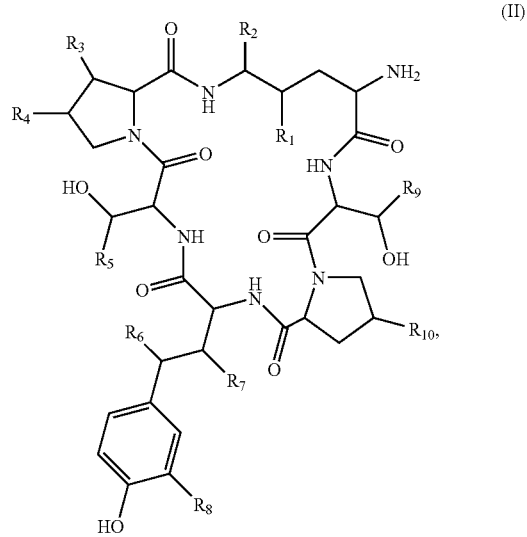

where $R_1$-$R_{10}$ have the meaning mentioned for formula (I), and where alkyl, alkenyl, alkadienyl and alkatrienyl groups, where present in compounds of formula (I) and (II), may be branched or straight-chain.

3. The method as claimed in claim 2, wherein the ($C_6$-$C_{24}$) alkyl in the radical $R_{11}$ of compound (I) is n-hexyl, n-octyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl, n-dicosanyl, 9,11-dimethyltridecanyl or 11-methyltridecanyl.

4. The method as claimed in claim 2, wherein $R_{11}$ in compound (I) is

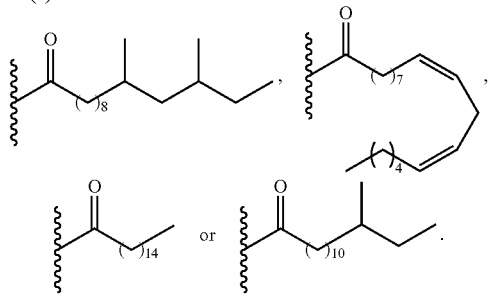

5. The method as claimed in claim 2, wherein the compound deoxymulundocandin (V) is prepared in step (a)

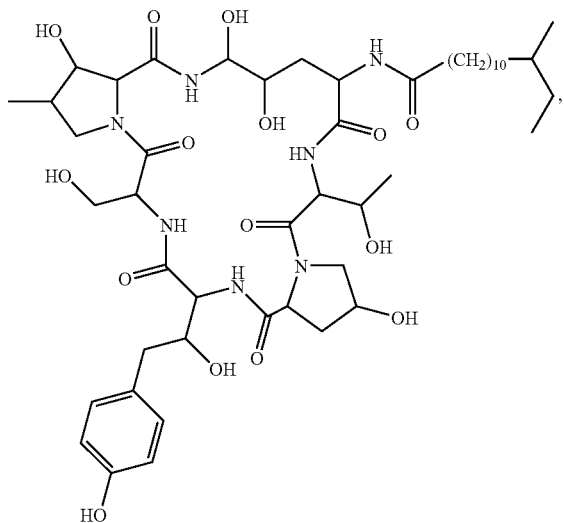

and the deoxymulundocandin nucleus (VI) is formed in step (c)

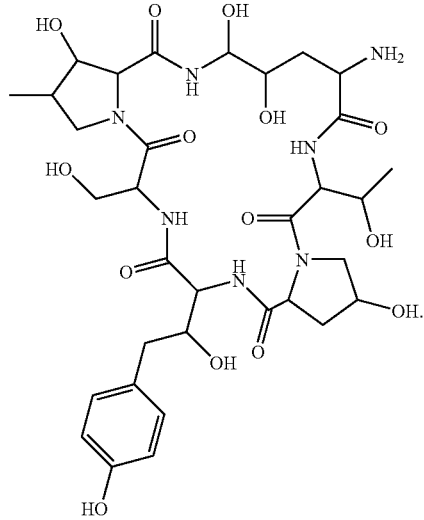

6. The method as claimed in claim 1, wherein the lipopeptide has the formula (III)

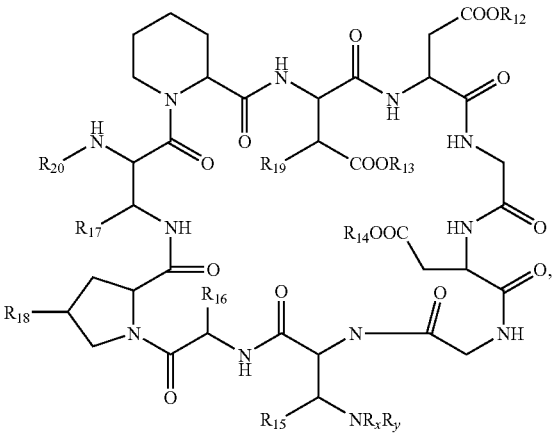

where $R_{12}$, $R_{13}$, $R_{14}$, $R_{15}$, $R_{16}$, $R_{17}$, $R_{18}$, $R_{19}$, $R_x$ and $R_y$, are, independently of one another, H or ($C_1$-$C_6$)alkyl, and $R_{20}$ is a C(O)—CH(CH$_2$COR$_{21}$)—NH—CO—($C_6$-$C_{24}$) alkyl group, a C(O)—CH(CH$_2$COR$_{21}$)—NH—CO—($C_6$-$C_{24}$)alkenyl group, a C(O)—CH(CH$_2$COR$_{21}$)—NH—CO—($C_6$-$C_{24}$)alkadienyl group, or a C(O)—CH(CH$_2$COR$_{21}$)—NH—CO—($C_6$-$C_{24}$)alkatrienyl group, where $R_{21}$ is OH or NH$_2$, and forms the corresponding nucleus of formula (IV)

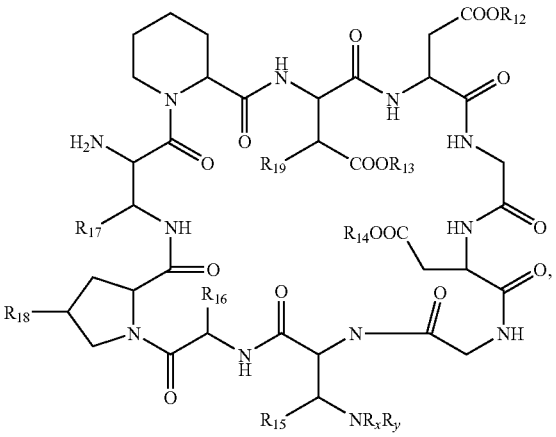

where $R_{12}$, $R_{13}$, $R_{14}$, $R_{15}$, $R_{16}$, $R_{17}$, $R_{18}$, $R_{19}$, $R_x$ and $R_y$ have the meaning mentioned above for formula (III), and where alkyl, alkenyl, alkadienyl and alkatrienyl groups, where present in compounds of formula (III) and (IV), may be branched or straight-chain.

7. The method as claimed in claim 6, wherein all of $R_{12}$, $R_{13}$, $R_{14}$, $R_{15}$, $R_{16}$, $R_{17}$, $R_{18}$, $R_{19}$, $R_x$ and $R_y$ are equal to H.

8. The method as claimed in claim 6, wherein $R_{20}$ is

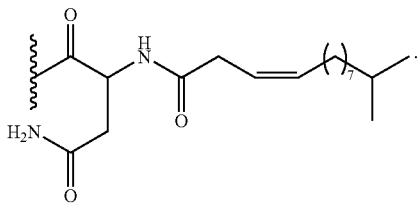

9. The method as claimed in claim 6, wherein the compound (VII) is prepared in step (a)

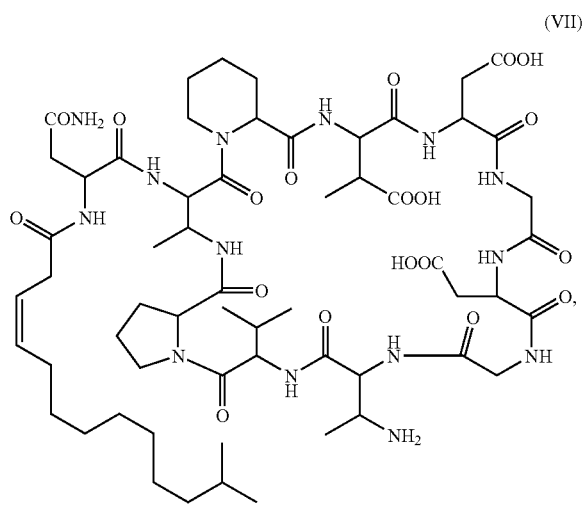

and the compound (VIII) is formed in step (c)

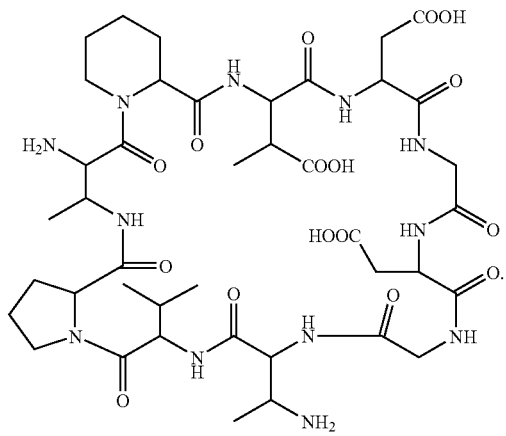

10. The method as claimed in claim 1, wherein the deacylase is obtained by cultivating *Actinoplanes utahensis*.

11. The method as claimed in claim 1, wherein the deacylase is obtained recombinantly by cultivating transformed *Streptomyces lividans*.

12. A method for preparing a semi-synthetic lipopeptide of formula (I')

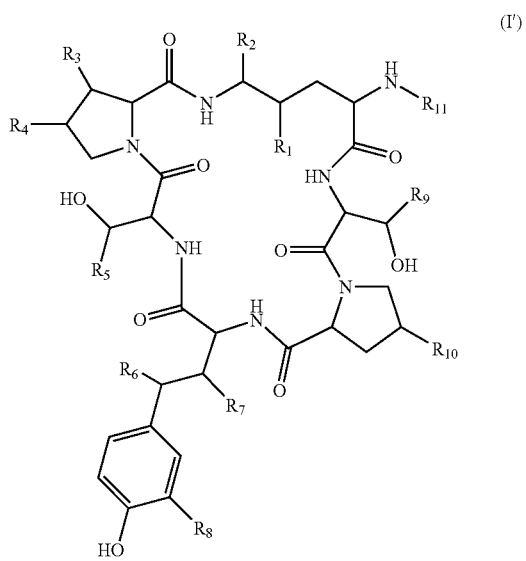

wherein
$R_1$ is H, OH or $NR_xR_y$, where
   $R_x$ and $R_y$, are, independently of one another, H or $(C_1-C_6)$ alkyl,
$R_2$ is H, OH, or $NH(CH_2)_2NH_2$,
$R_3$ is H, or OH,
$R_4$ is H, Me, $NH_2$, or $-NH-C(=NH)NH_2$,
$R_5$ is H, Me, $CH_2-C(=O)NH_2$, or $CH_2CH_2NH_2$,
$R_6$ is H, or OH,
$R_7$ is H, or OH,
$R_8$ is $OSO_3H$, $OSO_3Na$, or $NH-C(=O)CH_2NH_2$,
$R_9$ is Me,
$R_{10}$ is H, or OH, and
$R_{11}$ is a C(O)-phenyl-$(C_5-C_8)$heteroaryl-phenyl, 0(O)-biphenyl or
   C(O)-terphenyl group, comprising
(a) preparing a lipopeptide of formula (I)

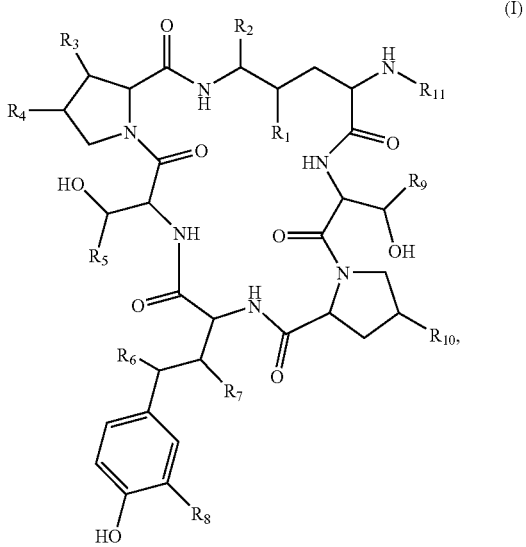

wherein $R_1$-$R_{10}$, $R_x$ and $R_y$ have the meanings given above and $R_{11}$ is a C(O)—($C_6$-$C_{24}$)alkyl group, a C(O)—($C_6$-$C_{24}$) alkenyl group, a C(O)—($C_6$-$C_{24}$) alkadienyl group, or a C(O)—($C_6$-$C_{24}$)alkatrienyl group, by fermentation, the lipopeptide (I) being bound to the cells of a biomass produced by the fermentation, and removing the biomass with the adhering lipopeptide of formula (I), (b) resuspending the biomass with the adhering lipopeptide of formula (I) from step (a) in an aqueous system, (c) adding a suitable deacylase which is capable of cleaving an N-acyl side chain in dissolved or solid form to the suspension of the biomass from step (b), and forming the corresponding nucleus of formula (II)

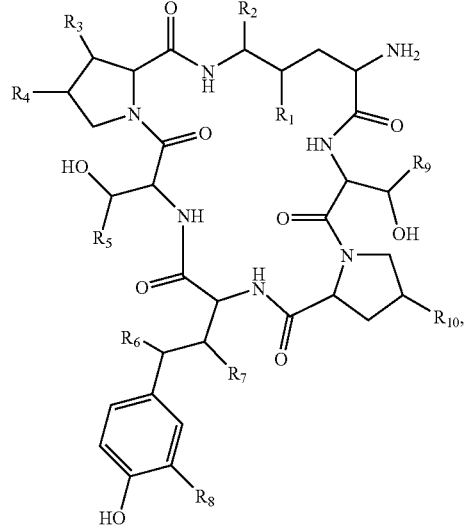

(II)

(d) optionally isolating and purifying the nucleus, and
(e) reacting the nucleus of formula (II) with an acid derivative of C(O)-phenyl-($C_5$-$C_8$)heteroaryl-phenyl, C(O)-biphenyl or C(O)-terphenyl to give the semi-synthetic lipopeptide of formula (I').

* * * * *